United States Patent
Sugita

[11] Patent Number: 5,314,439
[45] Date of Patent: May 24, 1994

[54] HOST CORNEA MARKING DEVICE
[75] Inventor: Juntaro Sugita, Nagoya, Japan
[73] Assignee: Menicon Co., Ltd., Japan
[21] Appl. No.: 968,592
[22] Filed: Oct. 29, 1992
[30] Foreign Application Priority Data Nov. 5, 1991 [JP] Japan .............................. 3-099371[U]

[51] Int. Cl.⁵ ................................................. A61F 9/00
[52] U.S. Cl. ..................................................... 606/166
[58] Field of Search ............... 606/166, 184, 167, 172, 606/116

[56] References Cited

U.S. PATENT DOCUMENTS

| | | | |
|---|---|---|---|
| 4,417,579 | 11/1983 | Soloviev et al. | 606/166 |
| 4,515,157 | 5/1985 | Fedorov et al. | |
| 4,619,259 | 10/1986 | Graybill et al. | |
| 4,796,623 | 11/1989 | Krasner et al. | 606/166 |

FOREIGN PATENT DOCUMENTS

| | | | |
|---|---|---|---|
| 2530948 | 2/1984 | France . | |
| 2590795 | 6/1987 | France . | |
| 854383 | 8/1981 | U.S.S.R. | 606/166 |
| 90/14808 | 12/1990 | World Int. Prop. O. . | |

OTHER PUBLICATIONS

Soviet Inventions Illustrated Section PQ, Week 8417, Derwent Publications Ltd., London, GB; Class P, AN 84-105529 & SU-A-1 016 881 (MOSC. Eye Microsurger.), Jun. 6, 1984.

Primary Examiner—Tamara L. Graysay
Attorney, Agent, or Firm—Parkhurst, Wendel & Rossi

[57] ABSTRACT

A host cornea marking device for providing marks on a recipient cornea bed of a corneal transplant patient is disclosed. The present marking device includes: an outer tube having a plurality of marking blades at one of opposite axial ends thereof which is adapted to face the recipient cornea bed, the marking blades being spaced apart from each other in a circumferential direction of said outer tube; and an inner tube which is received in the outer tube, such that the inner tube is axially slidable relative to the outer tube. The inner tube includes a contact portion at one of opposite axial ends thereof which is adapted to be in contact with the cornea bed so as to position the marking device with respect to a cutout section in the recipient cornea bed for receiving a donor cornea. A spring between the inner and outer tubes may be used to hold the inner tube in a first position.

6 Claims, 4 Drawing Sheets

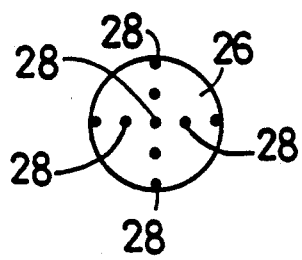
FIG. 5A
FIG. 5B
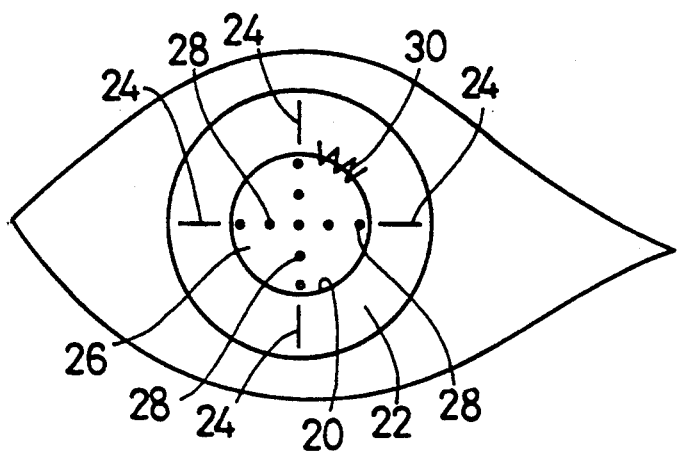
FIG. 6

HOST CORNEA MARKING DEVICE

BACKGROUND OF THE INVENTION

1. Field of the Invention

The present invention relates to a device for providing marks on a recipient cornea bed of a corneal transplant patient, for facilitating positioning of a donor cornea on the recipient cornea bed for keratoplasty.

2. Discussion of the Related Art

According to a known keratoplasty method, a suitable size of a section of the cornea of a corneal transplant patient (referred to hereinafter as a host patient) is cut out or removed, while a donor cornea is trephined or punched out by a suitable cornea punching device, so that the size of the donor cornea conforms to that of the cutout section of the host cornea. The thus obtained donor cornea is located on the cutout section of the host cornea and then sutured therein. Upon suturing, however, the cornea tends to be inadvertently distorted or displaced due to subtle differences in the manner of suturing from portion to portion, resulting in the incidence of post-transplant astigmatism due to such distortion of the cornea.

In view of the above situation, the inventor of the present invention proposed a cornea punching device as disclosed in co-pending U.S. patent application Ser. No. 07/682,695 now abandoned, for cutting or punching out a donor cornea into a desired shape, in preparation for keratoplasty. The punching device disclosed therein is adapted to cut out or trephine a circular corneal section such that the corneal section (hereinafter referred to as "donor cornea") is provided with a plurality of suction traces which correspond to suction holes or slits formed through a base for supporting the donor cornea when the donor cornea is punched out. More specifically, these suction traces are left on at least a peripheral portion of the surface of the donor cornea such that the traces are equally spaced apart from each other in the circumferential direction of the donor cornea. The thus formed suction traces can be used as a guide for positioning the donor cornea on a recipient cornea bed of a host patient, making it easy for an oculist to suture the graft with the cornea bed. It is thus possible to substantially avoid distortions of the cornea upon suturing, by advertently preventing inclination or displacement of the suction traces on the corneal graft.

Even if the donor cornea is provided by the above-described punching device with the suction traces for the positioning purpose, however, the positioning accuracy is still unsatisfactory in the absence of marks on the side of the host cornea or recipient cornea bed, which marks accurately correspond to the suction traces on the donor cornea. Consequently, there still remains a possibility of post-transplant astigmatism due to subtle distortion of the cornea grafted on the host patient.

SUMMARY OF THE INVENTION

It is therefore an object of the present invention to provide a marking device for providing marks on a host cornea or recipient cornea bed for keratoplasty, which marks accurately correspond to suction traces given on a donor cornea, and serve to effectively prevent distortions of the cornea upon suturing thereof, so as to avoid the incidence of post-operative astigmatism.

The above object may be attained according to the principle of the present invention, which provides a host cornea marking device for providing marks on a recipient cornea bed of a corneal transplant patient, comprising: an outer tube having a plurality of marking blades at one of opposite axial ends thereof which is adapted to face the recipient cornea bed, the marking blades being spaced apart from each other in a circumferential direction of the outer tube; and an inner tube which is received in the outer tube, such that the inner tube is axially slidable relative to the outer tube between a first position in which the inner tube protrudes a predetermined distance from the one of opposite axial ends of the outer tube, and a second position in which the inner tube is entirely positioned within the outer tube, the inner tube including a contact portion at one of opposite axial ends thereof which is to face the recipient cornea bed, the contact portion being adapted to be in contact with the cornea bed so as to position the marking device with respect to a cutout section in the recipient cornea bed for receiving a donor cornea.

In operation of the host cornea marking device constructed as described above, the inner tube is inserted into the cutout section formed in the recipient cornea bed of the host patient, so that the center of the marking device is accurately positioned on the center of the cornea cutout section. In this condition, the outer tube is pushed down so that the marking blades are lightly pressed against the recipient cornea bed, to thereby easily provide marks in the form of cuts in the host cornea. This permits extremely easy marking on the host cornea, while avoiding deviation of the center of the marking device, with the marks thus provide being accurately positioned relative to the periphery of the cutout section of the host cornea. If the spacing between the adjacent marking blades of the outer tube is determined so that the marks given by the blades are accurately aligned with corresponding suction traces which are left on the donor corneal graft, the marks and suction traces are advantageously used as a guide when the cornea is sutured, effectively preventing distortions of the cornea during the suturing operation, with a significantly lowered possibility of post-transplant astigmatism. Generally, the suction traces and marks given onto the cornea remain clearly visible for about 20 minutes, and then disappear by degrees, without causing any problem in a patient's vision or eyesight.

According to one feature of the invention, the host cornea marking device may further include biasing means, disposed between the outer tube and the inner tube, for normally holding under its biasing force the inner tube in the above-indicated first position, i.e., the position where the inner tube protrudes a given distance ahead of the above-indicated one axial end of the outer tube which is to face the cornea bed. In this arrangement, the inner tube, which has been retracted into the outer tube after the marking device is used, need not be moved out of the outer tube for subsequent use, assuring improved efficiency in the marking procedure.

BRIEF DESCRIPTION OF THE DRAWINGS

The above and optional objects, features and advantages of the present invention will be better understood by reading the following detailed description of presently preferred embodiments with the accompanying drawings, in which:

FIG. 5A and 5B are plan and front views showing a donor cornea with suction traces left on its surface, when the donor cornea is cut out by a cornea punching device;

FIG. 6 is a view showing the recipient eye of FIG. 4 along with the donor cornea of FIG. 5, when the donor cornea is sutured onto the cornea bed.

DETAILED DESCRIPTION OF THE PREFERRED EMBODIMENTS

Figure 1:
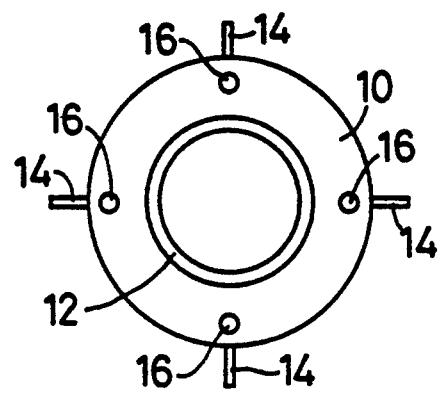
FIG. 1 is a plan view showing one embodiment of a host cornea marking device of the present invention.
Figure 2:
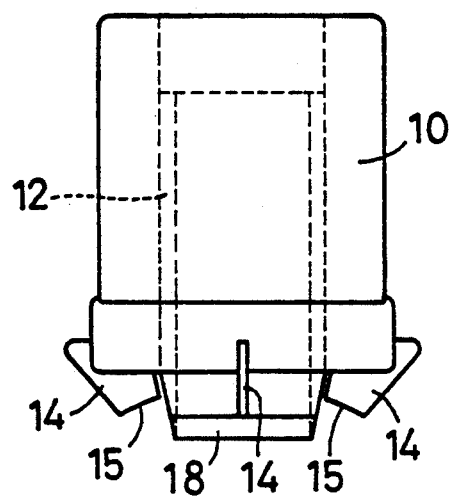
FIG. 2 is a front elevational view of the host cornea marking device of FIG. 1.

Referring first to FIGS. 1 and 2, there is illustrated one embodiment of a host cornea marking device of the present invention. In these figures, reference numeral 10 denotes an outer tube made of synthetic resin and having an outer diameter of 14 mm and a length of 19 mm. Within an inner bore of the outer tube 10, there is received an inner tube or centering tube 12 made of stainless steel and having an inner diameter of 7.5 mm and an outer diameter slightly smaller than the inner diameter of the outer tube 10. The centering tube 12 is axially slidable relative to the outer tube 10. That is, the centering tube 12 can smoothly move within the outer tube 10 when it is lightly pushed.

The outer tube 10 is provided at one axial end (lower end in FIG. 2) which is to face a cornea bed of a recipient eye, with four marking blades 14 in the form of stainless-steel razor blades, which are equally spaced apart from each other along the circumference of the tube 10, so as to correspond to suction traces 28 which are left on a donor cornea 26 as shown in FIG. 5A and 5B when the cornea 26 is trephined. These marking blades 14 are fixedly bonded to the outer tube 10 such that the blades 14 extend in radial directions of the outer tube 10. On the other axial end face of the outer tube 10 remote from the marking blades 14, there are provided four indicia 16 which are aligned with the marking blades 14, as shown in FIG. 1, for facilitating recognition of the positions of the blades 14.

More specifically, the outer tube 10 is formed of polymethyl methacrylate, and its inner circumferential surface is coated with grease so as to enhance slidability of the centering tube 12 received in the inner bore of the tube 10. The material for the outer tube 10 is not limited to polymethyl methacrylate (PMMA), but may be suitably selected from various plastics such as polycarbonate, polyacetal (POM) or fluororesin, or metals such as stainless steel. Alternatively, the outer tube 10 may have a dual-layer structure which consists of an inner layer made of plastics such as POM or fluororesin, which permits easy sliding of the centering tube 12, and an outer layer made of plastics such as PMMA. The dual-layer structure may also consist of an inner layer made of fluororesin or other plastics, and an outer layer made of a metal such as stainless steel. The marking blades 14 indicated above may be fixed to the outer tube 10 by a suitable method other than bonding, such as welding or soldering, depending upon the material of the outer tube 10.

The marking blades 14 have respective cutting edges 15 each having an arcuate shape which corresponds to the curvature of the cornea of the recipient eye, so as to give marks of even clearness (or depth) on the recipient cornea bed. The marking blades 14 are desirably attached to the outer tube 10 such that the blades 14 protrude at least 0.5 mm from the end face of the tube 10 toward the recipient cornea bed to be marked. In this embodiment, the marking blades 14 protrude about 1 mm from the outer tube 10.

In the instant embodiment, the four marking blades 14, which correspond to the suction traces 28 of the donor cornea 26 as shown in FIG. 5A and 5B, are attached to the outer tube 10 such that the blades 14 are equally spaced apart from each other in the circumferential direction of the tube 10. Thus, the number and positions of the marking blades 14 fixed to the outer tube 10 are determined so as to substantially correspond to those of the suction traces 28 of the donor corneal graft 26. While the number of the marking blades 14 is not particularly limited, it is preferably in a range of 2 to 12, more preferably, in a range of 3 to 8. It is also desirable that the marking blades 14 are disposed at the above-indicated one axial end of the outer tube 10 facing the recipient cornea bed, such that the blades 14 are substantially equally (equiangularly) spaced apart from each other in the circumferential direction. While the material and shape of the marking blades 14 are not particularly limited, stainless-steel razor blades as used in the instant embodiment are preferably used as the blades 14. It is also preferable that the marking blades 14 are fixed to the outer tube 10 so that the cutting edges 15 of the blades 14 extend in the radial directions of the tube 10.

Figure 3:
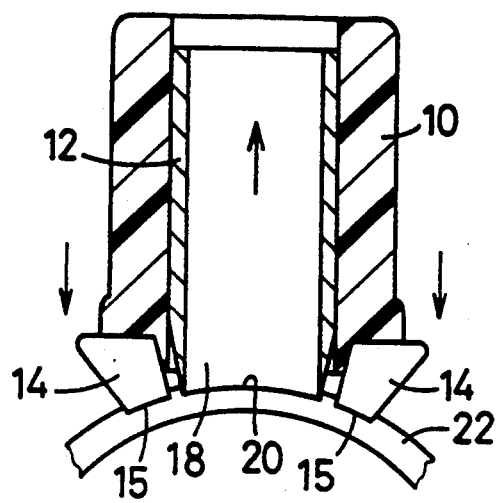
FIG. 3 is a cross sectional view showing the host cornea marking device when used on a recipient cornea bed of a host patient.

The centering tube 12 has a tapered portion 18 at its axial end facing the recipient cornea bed, for contact with the periphery of a circular cutout section 20 formed in the cornea of the host patient. The diameter of the tapered portion 18 is made substantially equal to that of the cutout section 20, as shown in FIG. 3. Accordingly, the tapered portion 18 of the centering tube 12 may be aligned with the cutout section 20 of the host cornea so as to achieve centering of the host cornea marking device during a marking operation. More specifically, the diameter of the tapered portion 18 is preferably held in a range of 5~11 mm. It is practically desirable to prepare several kinds of centering tubes 12 having different diameters, for example, 7.0 mm, 7.5 mm and 8.0 mm, which are selectively used depending upon the diameter of the cutout section 20. While the material for the centering tube 12 is not particularly limited, stainless steel as used in the instant embodiment is preferably used.

Various keratoplasty methods are generally known which include surface transplant, interlayer transplant and whole-layer transplant. The host cornea marking device constructed as described above may be used for the surface transplant or whole-layer transplant, to effect good marking on the host cornea.

In the surface transplant for transplanting only the front layer of the cornea, for example, the instant host cornea marking device is used in the following procedure:

(1) Initially, the centering tube 12 is pulled out of the outer tube 10, so that the tapered portion 18 protrudes ahead of the marking blades 14, as shown in FIG. 2.

(2) Then, the tapered portion 18 of the centering tube of the marking device is inserted into and held in place within the cutout section 20 formed by circularly cutting only the front layer of the host cornea 22, as shown in FIG. 3. At this point, the positions of the four marking blades 14 are easily recognized if the blades 14 are located at the 12, 3, 6 and 9 o'clock positions on the host cornea 22. Even where the marking blades 14 are hidden by a hand, the positions of the blades 14 can be easily recognized by the indicia 16 provided on the end face of the outer tube 10 remote from the marking blades 14.

(3) With the marking device thus being centered by means of the centering tube 12, the operator holding the outer tube 10 pushes down the tube 10 toward the host cornea 22. As a result, the centering tube 12 slides back into the outer tube 10, and the marking blades 14 are brought into contact with the cornea 22. In this state, the outer tube 10 is held lightly pushed toward the cornea 22 for a few seconds, to effect marking as shown in FIG. 3.

Figure 4:
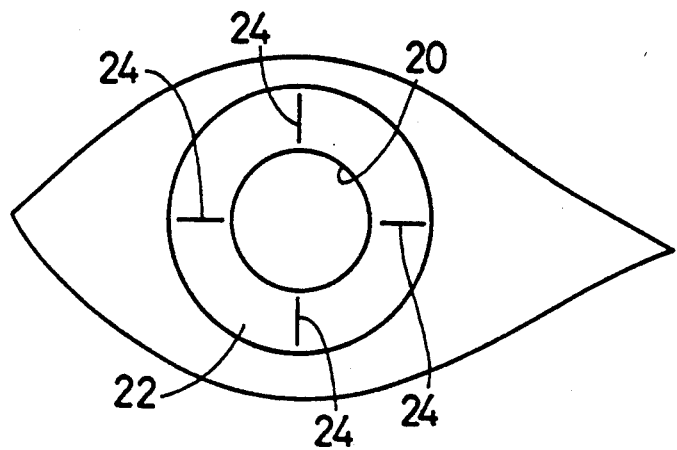
FIG. 4 is a plan view of a recipient eye including the cornea bed which is provided with marks by the marking device of FIG. 1.

(4) Thereafter, the host cornea marking device is removed from the host cornea 22, on which there have been formed four marks 24 which extend in the respective 90°-spaced radial directions, as shown in FIG. 4.

(5) On the host cornea 22 provided with the marks 24 in the manner as described above, there is located the donor cornea 26 provided with the suction traces 28 which collectively form a cross as shown in FIG. 5A and 5B. The donor corneal graft 26 and host cornea 22 are then sutured with thread 30, such that the suction traces 28 on the cornea 26 are aligned with the marks 24 on the host cornea 22, as shown in FIG. 6. In this connection, the donor cornea 26 may be cut out for use in this transplant, by means of a cornea punching device as disclosed in the above-identified U.S. patent application Ser. No. 07/682,695 now abandoned.

The use of the host cornea marking device as described above ensures that the host cornea 22 is provided with high reliability with the marks 24, which are accurately aligned with the suction traces 28 of the donor cornea 26, with extremely easy handling of the device. When the donor cornea 26 and host cornea 22 are sutured with their traces 28 and marks 24 aligned with each other, distortions of the cornea 26 which would otherwise occur upon suturing can be reduced to a minimum, with the least possibility of post-transplant corneal astigmatism.

Figure 7:
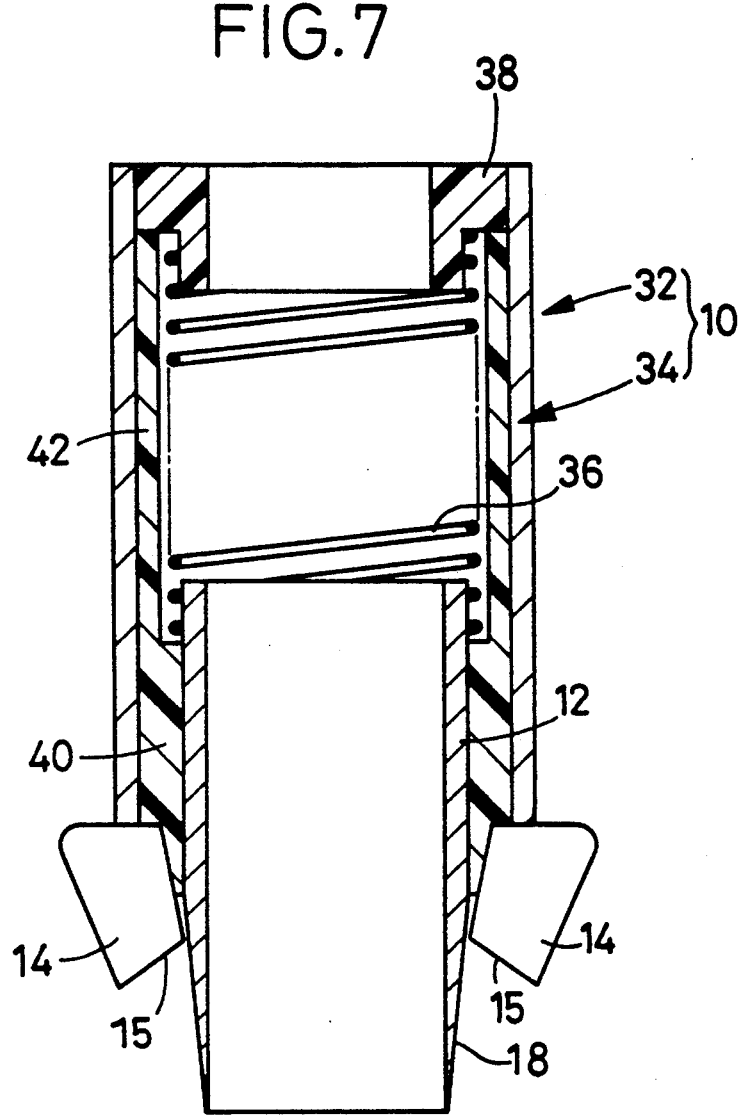
FIG. 7 is a cross sectional view showing another embodiment of the host cornea marking device of the present invention.

Referring next to FIG. 7, there is illustrated another embodiment of the host cornea marking device of the present invention. In this embodiment, the outer tube 10 has a dual-layer structure which consists of an outer layer 32 made of stainless steel, and an inner layer 34 made of fluororesin. The centering tube 12 is received in the outer tube 10 such that it is slidable on the inner layer 34. Between the outer tube 10 and the centering tube 12, there is provided biasing means in the form of a spring 36, which serves to keep the centering tube 12 in a predetermined position at which the tapered portion 18 protrudes a suitable distance from the outer tube 10.

The spring 36 is mounted on the device such that one end of the spring 36 is fixedly wound around the axial end portion of the centering tube 12 remote from the tapered portion 18, and such that the other end thereof is secured to an annular spring seat 38 made of fluororesin, which is fixedly fitted in the axial end portion of the outer tube 10 remote from the marking blades 14. The inner layer 34 of the outer tube 10 consists of a first section 40 for slidably receiving the centering tube 12, and a second section 42 for accommodating the spring 36. The first section 40 corresponds to the axial end portion of the tube 10 facing the recipient cornea bed, over about one-third of the entire length of the tube 10, while the second section 42 constitutes the rest of the inner layer 34, and has a larger diameter than the first section 40. In this arrangement, the centering tube 12 is favorably prevented from rattling in the outer tube 10, while permitting free movement of the spring 36.

In operation of the thus constructed host cornea marking device, the outer tube 10 is pushed down to the host cornea 22, against a biasing force of the spring 36, to accomplish good marking on the host cornea 22. Then, the centering tube 12, which has been retracted into the outer tube 10 upon marking, resumes its original position, that is, returns to the above-indicated predetermined position where the centering tube 12 protrudes a suitable distance from the outer tube 10. Accordingly, the centering tube 12 need not be pulled out of the outer tube 10 by hand each time the device is used for marking the cornea. Further, since the outer layer 32 of the outer tube 10 of the instant marking device is made of stainless steel as described above, the marking blades 14 can be firmly secured to the outer layer 32 by soldering.

While the present invention has been described in detail in its presently preferred embodiments, for illustrative purpose only, it is to be understood that the invention is by no means limited to the details of the illustrated embodiments, but may be embodied with various other changes, modifications and improvements, which may occur to those skilled in the art, without departing from the scope of the invention defined in the appended claims.

What is claimed is:

1. A host cornea marking device for providing marks on a recipient cornea bed of a corneal transplant patient, said cornea bed having a cutout section, said host cornea marking device comprising:

an outer tube having a plurality of marking blades at one of opposite axial ends thereof which is adapted to face the recipient cornea bed, said marking blades being spaced apart from each other in a circumferential direction of said outer tube;

an inner tube which is received in said outer tube, such that said inner tube is axially slidable relative to the outer tube during a marking operation between a first position in which the inner tube protrudes a predetermined distance from said one of opposite axial ends of the outer tube and axially past the marking blades, and a second position in which the inner tube is entirely positioned within the outer tube; and positioning means for positioning the marking device with respect to the cutout section in the recipient cornea bed for receiving a donor cornea, said positioning means comprising a contact portion of one of opposite axial ends of the inner tube, said contact portion being adapted to fit within the cutout section and adapted to be in contact with the cornea bed so as to position the marking device.

2. A host cornea marking device according to claim 1, further comprising biasing means, disposed between said outer tube and said inner tube, for normally holding said inner tube in said first position under a biasing force thereof.

3. A host cornea marking device according to claim 1, wherein said contact portion of said inner tube is tapered such that a diameter of the contact portion decreases toward said one of opposite axial ends of the inner tube which is adopted to contact the recipient cornea bed.

4. A host cornea marking device according to claim 1, wherein said marking blades extend in radial directions of said outer tube.

5. A host cornea marking device according to claim 1, wherein said marking blades are equally spaced apart from each other in the circumferential direction of said outer tube.

6. A host cornea marking device according to claim 1, wherein said marking blades are made of stainless steel.

* * * * *